(12) United States Patent
Bohle

(10) Patent No.: US 8,649,009 B2
(45) Date of Patent: Feb. 11, 2014

(54) OPTICAL SPECTROMETER ELEMENT HAVING NON-SPHERICAL MIRRORS

(75) Inventor: Wolfram Bohle, Kleve (DE)

(73) Assignee: Spectro Analytical Instruments GmbH, Kleve (DE)

( * ) Notice: Subject to any disclaimer, the term of this patent is extended or adjusted under 35 U.S.C. 154(b) by 741 days.

(21) Appl. No.: 12/663,619

(22) PCT Filed: Jun. 4, 2008

(86) PCT No.: PCT/EP2008/004489
§ 371 (c)(1),
(2), (4) Date: Jan. 19, 2010

(87) PCT Pub. No.: WO2008/148551
PCT Pub. Date: Dec. 11, 2008

(65) Prior Publication Data
US 2010/0141941 A1    Jun. 10, 2010

(30) Foreign Application Priority Data
Jun. 8, 2007    (DE) .......................... 10 2007 027 010

(51) Int. Cl.
*G01J 3/28*    (2006.01)
(52) U.S. Cl.
USPC ....................................................... 356/328
(58) Field of Classification Search
USPC ............................................... 356/317, 326
See application file for complete search history.

(56) References Cited

U.S. PATENT DOCUMENTS

| 4,049,353 | A | * | 9/1977 | Missio | 356/310 |
| 4,575,241 | A | * | 3/1986 | Demers et al. | 356/316 |
| 5,018,856 | A | * | 5/1991 | Harnly et al. | 356/312 |
| 5,963,320 | A | * | 10/1999 | Brooks et al. | 356/310 |
| 6,392,748 | B1 | * | 5/2002 | Fateley | 356/330 |
| 6,862,092 | B1 | * | 3/2005 | Ibsen et al. | 356/328 |
| 2006/0092414 | A1 | | 5/2006 | Geshwind et al. | |

FOREIGN PATENT DOCUMENTS

| DE | 19853754 A1 | 5/2000 |
| DE | 102005057919 A1 | 6/2007 |
| JP | 10111176 A | 4/1998 |

OTHER PUBLICATIONS

English language International Preliminary Report on Patentability and Written Opinion issued in related International Application No. PCT/EP2008/004489 on Jan. 12, 2010.

* cited by examiner

*Primary Examiner* — Tarifur Chowdhury
*Assistant Examiner* — Abdullahi Nur
(74) *Attorney, Agent, or Firm* — Novak Druce Connolly Bove + Quigg LLP

(57) ABSTRACT

The invention relates to a spectrometer for analyzing the optical emission of a sample, having an excitation source, an entrance gap and a dispersive element, which fans out the spectrum of the light generated in the excitation source in a plane, and having solid body sensors with one or more lines, which are arranged in the region of the focal curve of the beam path in order to evaluate the spectral information, wherein the sensors are arranged above or below the plane and the spectral emission is deflected onto the sensors by mirrors and focused, wherein the reflecting surface of the mirrors is aspherically formed in a direction of curvature.

6 Claims, 1 Drawing Sheet

OPTICAL SPECTROMETER ELEMENT HAVING NON-SPHERICAL MIRRORS

CROSS-REFERNCE TO RELATED APPLICATIONS

Figure 1:
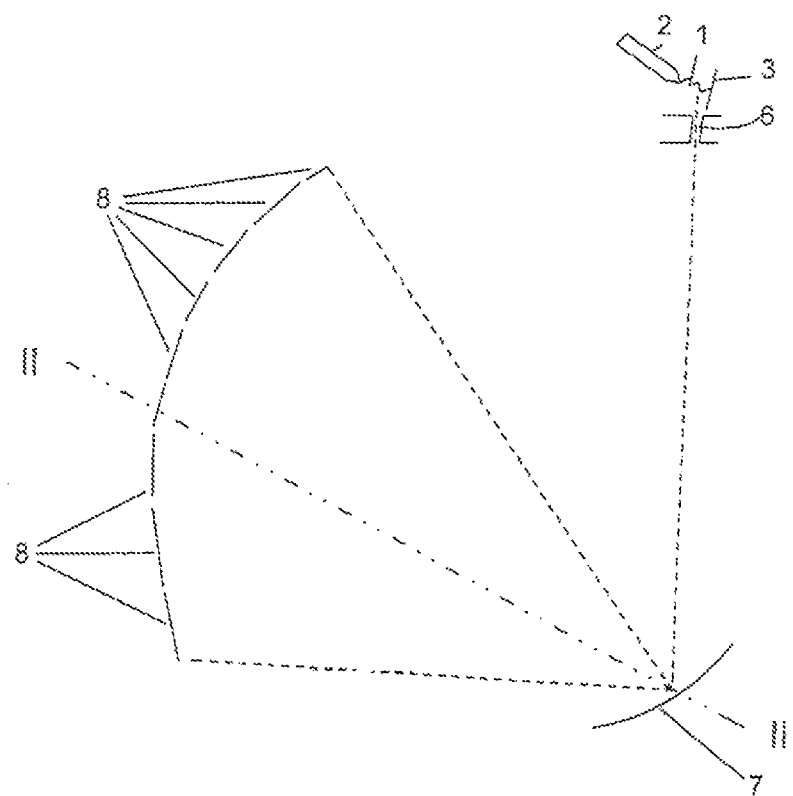

This application is a 35 U.S.C. 371 National Stage Application of International Application No. PCT/EP2008/004489, filed Jun. 5, 2008, which claims priority from German Application No. 102007027010.2, filed Jun. 8, 2007, the entire contents of which are incorporated herein by reference.

The present invention relates to a spectrometer for analysing the optical emission of excited samples in the range of visible wavelengths and adjacent wavelength ranges having the features of the preamble of claim 1.

In the case of generic spectrometers, part of a sample is evaporated by sparks, arcs or ICP and changed into plasma. The emissions of the plasma contain spectral lines of the elements occurring therein which can be analysed with optical spectrometers. The light to be analysed enters via an entrance gap into a spectrometer housing, is diffracted there on a dispersive element and spectrally fanned out. The spectral lines develop as imaging of the entrance gap on a so-called focal curve. Detectors, with which the light of the interesting wavelength range is collected and evaluated, are arranged on this focal curve. In many cases, spatially resolving semiconductor detectors, which consist of a line of detector elements of the CCD or CMOS design, are used. These lines of detectors are not arranged directly on the focal curve for various reasons but, in relation to the plane of the beam path, above or below the focal curve. The light in the case of known spectrometers of this design is deflected by cylindrical mirrors from the plane of the beam path and focused onto the lines of detectors below this plane. In this case, the cylindrical mirrors are straight in their longitudinal extension and spherical in their direction of curvature. These are mirrors made of glass which have a highly reflective surface.

In practice, it has been shown that although spectrometers constructed in this way perform well optically, the light yield, i.e. the amount of light present in the beam path of a certain wavelength, which actually reaches the detector, is not optimum for weak emission lines.

The object of the present invention is, therefore, to create a spectrometer of the design mentioned at the beginning, in which the light yield is improved.

This object is achieved by a spectrometer having the features of claim 1.

Because the focusing tilted mirrors have an aspheric surface, their imaging characteristics are better adapted to the geometrical conditions in such a spectrometer. Preferably, a surface which perpendicular to the plane of the beam path corresponds to the mathematical shape of a parabola is selected in this case. Provision may also be made for the surface to be formed from a section of an ellipse.

Figure 2:
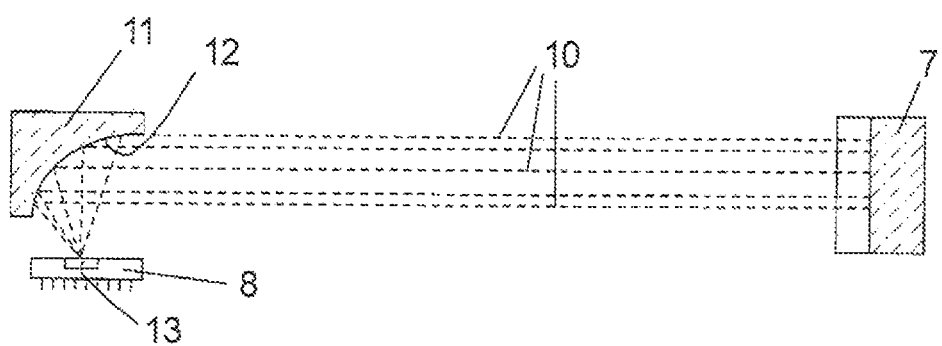

The present invention is described below by means of the drawing, wherein:

FIG. 1 shows a schematic layout of a spectrometer having line sensors in a top view onto the plane of the beam path; and FIG. 2 shows a sectional view through the schematically represented spectrometer along the line II-II.

FIG. 1 schematically shows the beam path of a spectrometer with spark excitation. An electrical spark 1 is generated between an electrode 2 and a sample 3. The spark causes an emission in the UV range and in the visible light range with the characteristic spectral lines of the chemical elements contained in the sample 3. The light is guided through an entrance gap 6 into the interior of the spectrometer and there strikes a diffraction grating 7, which spectrally fans out the light in one plane and images the entrance gap 6 onto lines of solid body sensors 8. Preferably, such a spectrometer, in the case of mass-produced devices for laboratory and industrial purposes, is constructed in a Paschen-Runge arrangement.

The beam path between the diffraction grating 7 and the sensors 8 is illustrated in more detail in FIG. 2. Here, schematically the concave diffraction grating 7 is illustrated as a cross section from which a number of beams 10 run parallel to one another onto an imaging mirror 11. The imaging mirror 11 has a surface 12 turned towards the beams 10, which has a highly-reflective surface and whose curvature runs aspherically, i.e. in this exemplary embodiment corresponds to a parabola section. The reflecting surface 12 focuses the light beams 10 onto a light-sensitive element 13 of the CCD sensor line 8. The light yield is substantially improved in the case of this geometric arrangement in contrast to known spectrometers, in which the light beams 10 are to be focused via cylindrical mirrors onto the CCD line 8.

Additionally, a smaller amount of scattered light results in the spectrometer due to improved bundling of the emission.

In the case of another embodiment (not illustrated), the curvature of the aspherical surface 12 of the mirror 11, perpendicular to the spectral plane, can also assume the shape of an elliptic section.

The mirror 11 is linear in the direction perpendicular to the plane of projection in FIG. 2, which enables the mirror 11 to be manufactured relatively simply. The manufacture of the mirror 11, and in particular the moulding of the surface shape in the region of the highly-reflective surface 12, is preferably carried out using glass in a moulding process, in which the mould is removed from a matrix. The resulting glass moulding can be finished to form a mirror by cutting to size, carrying out vapour deposition for example with aluminum and mounting in a frame, as is required for the present invention.

The invention claimed is:

1. A spectrometer for analyzing the optical emission of a sample having: an excitation source, an entrance gap, a dispersive element configured to fan out the spectrum of the light generated in the excitation source in a plane, a plurality of optical solid body sensors, which are arranged in the region of the focal curve of the beam path in order to evaluate the spectral information, wherein the sensors are arranged above or below the plane, and a plurality of mirrors configured to deflect the spectral emission and to focus the spectral emission onto the sensors, wherein the reflecting surfaces of the mirrors are aspherically formed in a direction of curvature, wherein at least one of the sensors is arranged with a sensing component oriented substantially parallel to the plane, and wherein at least one of the mirrors is configured to deflect at least a portion of the spectral emission from the plane, in a direction perpendicular to the plane, onto the sensing component.

2. The spectrometer according to claim 1, wherein the reflecting surfaces in one direction correspond to a parabola section.

3. The spectrometer according to claim 1, wherein the curvature in one direction corresponds to an elliptic section.

4. The spectrometer according to claim 1, wherein the reflecting surfaces, perpendicular to the direction of curvature, are linearly formed.

5. The spectrometer according to claim 1, wherein the solid body sensors with detector elements are used in a line.

6. The spectrometer according to claim 1, wherein the solid body sensors with detector elements are used in a plurality of lines.

\* \* \* \* \*